United States Patent [19]

Mollot et al.

[11] Patent Number: 4,948,552
[45] Date of Patent: Aug. 14, 1990

[54] ULTRASONIC WAVE SENSOR INTENDED TO COME INTO CONTACT WITH A WALL AT A HIGH TEMPERATURE AND APPLICATION OF THIS SENSOR

[75] Inventors: Christian Mollot, Paris; Jacques Malmasson, Evry, both of France

[73] Assignee: Framatome, Courbevoie, France

[21] Appl. No.: 119,275

[22] Filed: Nov. 6, 1987

Related U.S. Application Data

[63] Continuation-in-part of Ser. No. 839,291, Mar. 13, 1986, abandoned.

[30] Foreign Application Priority Data

Mar. 15, 1985 [FR] France ................ 85 03871

[51] Int. Cl.[5] .......................................... G21C 17/02
[52] U.S. Cl. ........................................ 376/246; 73/644
[58] Field of Search ............... 73/861.27, 861.28, 644; 376/246, 249

[56] References Cited

U.S. PATENT DOCUMENTS

| | | | |
|---|---|---|---|
| 2,515,221 | 7/1950 | Henning | 73/861.27 |
| 3,575,050 | 4/1971 | Lynnworth | 73/861.28 |
| 3,934,457 | 1/1976 | Clark et al. | 376/249 |
| 4,195,517 | 4/1980 | Kaliwosk | 73/861.28 |
| 4,392,380 | 7/1983 | Caines | 73/644 |
| 4,422,340 | 12/1983 | Kolodzey et al. | 376/246 |
| 4,454,767 | 6/1984 | Shinkai et al. | 73/861.28 |
| 4,783,997 | 11/1988 | Lynnworth | 73/644 |

FOREIGN PATENT DOCUMENTS

| | | | |
|---|---|---|---|
| 64984 | 5/1977 | Japan | 73/644 |
| 152296 | 8/1985 | Japan | 73/644 |
| 2060884 | 5/1981 | United Kingdom. | |
| 2086183 | 5/1982 | United Kingdom. | |

OTHER PUBLICATIONS

IBM Tech. Discl. Bull., vol. 15, No. 1, (6/72), pp. 309–310, Ash et al.

Primary Examiner—Deborah L. Kyle
Assistant Examiner—Richard W. Wendtland
Attorney, Agent, or Firm—Pollock, Vande Sande & Priddy

[57] ABSTRACT

The ultrasonic wave sensor (2) according to the invention comes into contact with a wall at a high temperature (1) by means of a wave guide (5) made of a vitroceramic material. The sensor includes, inside a body (3) made of metallic material, a piezoelectric ceramic pellet (8) connected to an electrical power supply or measurement leads (9). The wave guide (5), also placed in the body (3), is in contact by one of its ends (5b) with the piezoelectric pellet (8) and by its other end (5a) with the wall (1). The body (3) of the sensor is mounted in an articulated manner on a support (21) fixed to the wall (1). The invention applies in particular to the measurement of flow rate in a primary duct of a pressurized-water nuclear reactor.

9 Claims, 2 Drawing Sheets

ULTRASONIC WAVE SENSOR INTENDED TO COME INTO CONTACT WITH A WALL AT A HIGH TEMPERATURE AND APPLICATION OF THIS SENSOR

This application is a continuation-in-part of application Ser. No. 839,291, filed Mar. 13, 1986, now abandoned.

FIELD OF THE INVENTION

The invention relates to an ultrasonic wave sensor intended to come into contact with a wall at a high temperature, and applications of this sensor, particularly to flow rate measurements.

BACKGROUND OF THE INVENTION

In industrial installations in which high temperature fluids circulate in ducts, it is very often necessary to measure the velocity or flow rate of those fluids in order to control or monitor the industrial installation. For example, in the case of nuclear power stations incorporating a pressurized-water reactor, it is necessary to know the flow rate of the primary water to a very high degree of accuracy while the reactor is operating. The flow rate can be measured by determining the velocity of propagation of the pressurized water in a primary duct, by measuring the the propagation time of ultrasonic waves in fluid circulating in the duct. In order to do this, use is made of ultrasonic sensors, which can transmit waves into the circulating water and receive these waves after propagation and possible reflection on a wall of the ducting. Prior art sensors actually have to be placed in an opening machined on the inside of the wall of the duct, to limit losses and amplify the amplitude of the received return echo.

Such a sensor mounting, which is described as intrusive in the duct makes the use of these sensors very difficult in the primary circuit of a pressurizedwater nuclear reactor in which the water is at a pressure of the order of $155 \cdot 10^5$ Pa and at a temperature in the range 280° C. to 320° C. For safety reasons it is in fact necessary to limit as far as possible the number of tappings in the primary ducts of the reactor.

Also, sensors which incorporate a piezoelectric ceramic pellet and a wave guide coupled to that pellet use in their manufacture materials that are generally incapable of withstanding the very high temperatures of the fluid and of the primary ducting.

In the case of a non-intrusive mounting of the sensor, the latter must, however, be in contact, via its wave guide, with the duct wall which is at a very high temperature. Consequently, the wave guide must be designed so as to withstand the temperature without distorting and without excessive expansion, and in such a way that it has a homogeneous, resonant and easily machinable structure, so that its surface coming into contact with the duct wall has a very high surface finish, i.e., of very low roughness. No wave guides having all these characteristics have been known to date.

SUMMARY OF THE INVENTION

The purpose of the invention is therefore to propose an ultrasonic wave sensor intended to come into contact with a wall at a high temperature, incorporating, within a body make of a metallic material connected to a support for positioning the sensor on the wall, a piezoelectric ceramic pellet connected an electrical power supply or measuring leads, and placing in contact with one end of a wave guide the other end of which is in contact with the wall when the sensor is in operating position, a sensor which does not have the disadvantages of the devices according to the prior art.

For this purpose, the waveguide consists of a single part made of a vitro-ceramic material, whose end in contact with the wall is machined to a very high surface finish.

BRIEF DESCRIPTION OF THE DRAWINGS

In order that the invention may be more clearly understood, a description will now be given, by way of example, with reference to the appended drawings, of an ultrasonic wave sensor according to the invention and its application to the measurement of the flow rate of pressurized water in a primary ducting of a pressurized-water nuclear reactor.

DESCRIPTION OF PREFERRED EMBODIMENT

Figure 1:
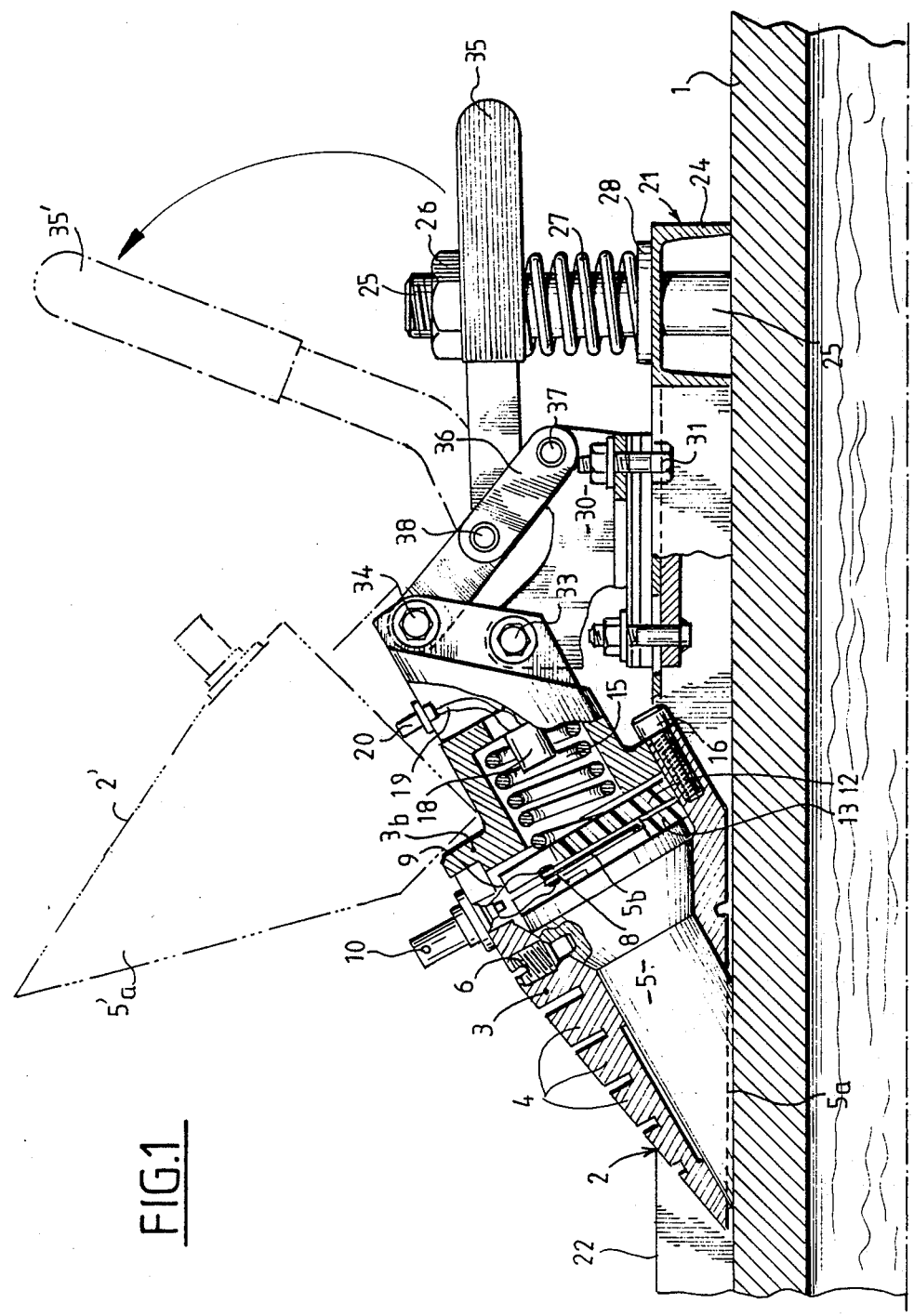
FIG. 1 is a cross-sectional view of the sensor in operating position on a primary duct of a pressurizedwater nuclear reactor.

FIG. 1 shows a primary duct 1 of a pressurized-water nuclear reactor on the outer wall of which has been fixed an ultrasonic sensor represented in solid lines in its operating position and in dot-and-dash lines in its non-operating position 2', in which the lower surface of the sensor is accessible.

The sensor 2 incorporates a metallic body 3 the front part of which is machined in order to form cooling fins 4. Inside this section of the metal body 3 is arranged the wave guide 5 coming into contact by its surface 5a with the outer surface of the duct 1, filled with water at a temperature of about 300° C. The wave guide 5 is fixed in the body 3 by a screw 6. The end surface 5b of the wave guide 5 away from surface 5a is in contact with a piezoelectric pellet 8 which can be connected by means of electrical leads 9 and a fast-connection terminal 10 to an electrical power supply source and/or to an installation for the retrieval and processing of the signals emitted by the piezoelectric cell 8.

This cell 8 is held in contact with the machined surface 5b of the wave guide 5 at the end of a reduced diameter cylindrical projection of that wave guide by a stop 12 and a centering washer 13 made of material sold under the trade name Permaglass. The centering washer 13 has a thickness greater than the thickness of the cylindrical projection on which the bearing surface 5b of the insert 8 is machined and very slightly less than the sum of the thicknesses of this cylindrical section of the wave guide and of the pellet 8. The stop 12 is pressed against the pellet 8 by a spring 15, held inside the rear part 5b of the metallic body of the sensor, fixed to the front part of this body by means of screws such as 16. The pellet 8 is thus held firmly against the surface 5b of the wave guide 5.

A Peltier effect cell 18 is fitted in part 3b of the metallic body 3, this capsule being supplied with electrical current by means of wires 19 and a fast connection terminal 20. This Peltier effect capsule makes it possible to restrict the temperature inside the metallic body 3 when the sensor is put into operation, as shown in FIG. 1, on a high temperature wall.

The end of the rear part 3b of the metallic body incoporates two holes making it possible to connect the metallic body 3, in an articulated manner, to a support designated generally by reference 21. This support 21 will be described with reference to FIGS. 1 and 2.

The support 21 incorporates two beam sections 22 bearing on the outer surface of the ducting 1, near its upper part, by contact members 23. Beam sections 24 having U-shaped cross sections are fixed at right angles to the beam sections 22 at one of their ends. The beam sections 24 are bored with holes permitting the passage of the ends of a fixing collar 25 the ends of which are threaded to receive a clamping nut 26 fixing the ends of the collar 25 onto the beam sections 24 by means of a spring 27 and a washer 28. On the two parallel beam sections 22 arranged in line with the longitudinal direction of the duct 1 is fixed a support 30 by means of screws 31, which can be seen on FIG. 1. The support 30 incorporates holes permitting the articulated fixing of the body 3 of the sensor. This body 3 is articulated on the support by means of an articulation 33 having a horizontal axis and on the end of an operating lever 35 by means of an articulation 34, also with a horizontal axis. The lever 35 is itself articulated on the support 30 by means of a link 36. The link 36 is articulated on the support 30 by means of an articulation 37 and on the handle 35 by means of an articulation 38, all the articulations having parallel axes. This assembly enables the sensor 2 to be put in its non-opert ing position 2' by raising the handle of the lever 35 from its position represented in solid lines in FIG. 1 to its position 35' represented in a dot-and-dash lines. It is thus easily possible to gain access to the lower surface of the sensor which comes into contact with the duct 1 in operating position.

Figure 2:
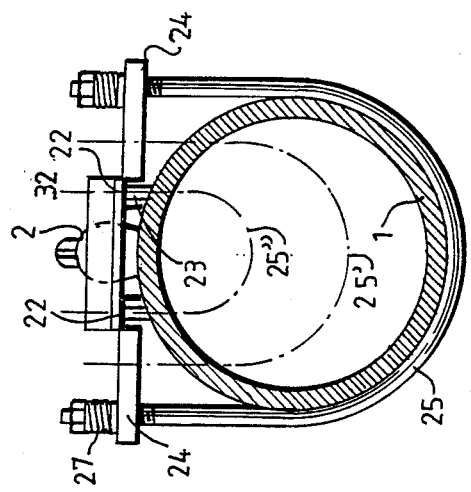
FIG. 2 is a view from along line A—A of FIG. 3, on a reduced scale, of the sensor in operating position.

FIG. 2 shows the positions 25' and 25" of a fixing collar in the case of ducts of decreasing diameters.

The wave guide 5 providing the coupling between the piezoelectric ceramic pellet 8 and the duct 1 must provide perfect coupling, in particular when measurements are to be made in the liquid environment filling the duct. This wave guide must therefore be made of a material having a structure that is homogeneous and resonant, and must be capable of being easily machined so that its surface 5a bearing against the wall in which the measurement is made has a perfect surface finish. This surface finish with very low roughness, obtained by polishing, must be similar to a mirror polish.

In addition, the wave guide must withstand the high temperatures transmitted by the wall of the duct without distortion or excessive expansion.

None of the known materials for the manufacture of wave guides meets these requirements.

The wave guide 5 has been manufactured in a vitroceramic material sold under the trade name Macor by the Corning Glass Company. This material has the following approximate composition:

Silica $SiO_2$ : 46%
Alumina $Al_2O_3$ : 16%
Magnesia $MgO$ : 17%
Potassium oxide $K_2O$ : 10%
Boron oxide $B_2O_3$ 7%
Flourine 4%

Such vitroceramic materials therefore have a composition close to that of glass, and their manufacture and shaping can be carried out using glass manufacturing techniques.

However, after the part has been shaped, it is subjected to heat treatments permitting limited development of crystals within the vitreous mass. This development of crystals is promoted by nucleating agents introduced into the fused material.

Such vitroceramic materials, the composition of which can vary widely, are well known, but have never been used for the production of wave guide making a coupling between a piezoelectric pellet and a high temperature wall.

The wave guide 5 was produced by casting and then crystallization heat treatment of a single part having the indicated composition, then by finishing machining of this part, in particular to produce the bearing surfaces 5a and 5b with a very high surface finish.

This machining of the wave guide, in the case of small diameter ductings, comprises a grinding of the bearing surface 5a of the wave guide in order to make this bearing surface cylindrical. In the case of large diameter ductings, the contact is made along a generatrix of the ducting, the bearing surface 5a being plane.

Wave guide made of vitroceramic material have all the characteristics required for the transmission of ultrasonic waves through a wall at a high temperature, but, at the same time, the material, because of its homogeneity and density, has a relatively high thermal transmission coefficient. This is why, within the metallic body 2, there is provided a Peltier effect capsule 18 which is powered in such a way as to cause an endothermic effect restricting the temperature inside the body of the sensor.

It is that capsule, it is possible to restrict the temperature to about 40° C. in the body of the sensor with a temperature of about 120° C. at the interface 5b between the wave guide 5 and the piezoelectric pellet 8, in the case of a wall 1 at a temperature of about 320° C., which is the maximum temperature of the primary fluid of a pressurized-water nuclear reactor.

It should be noted that the metal body 2 does not come into direct contact with the wall 1, this contact being provided solely by the end of the wave guide 5. The coupling between the wave guide and the ducting 1 can be improved by using a viscous coupling material, for example of the type consisting of an organic agent filled with nickel particles. Such a viscous coupling material is available commercially under the name Never Seez.

Figure 3:
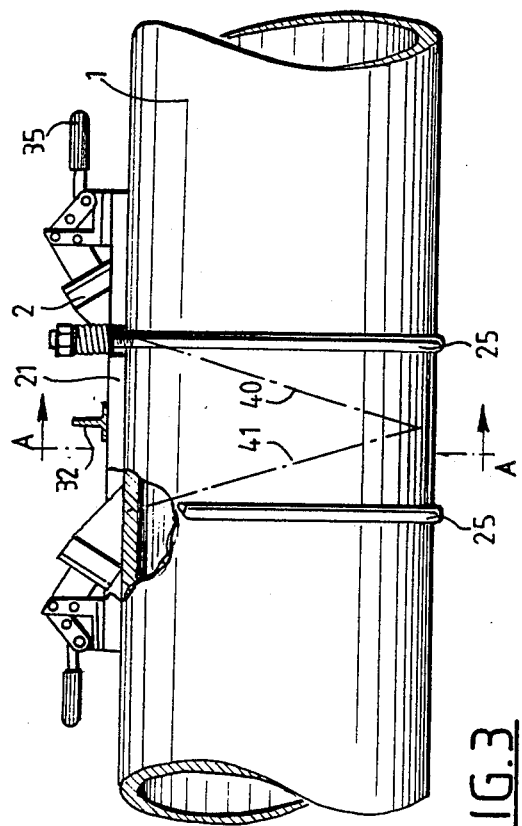
FIG. 3 is a perspective view of a set of two sensors according to the invention which are placed on a duct of the primary circuit of a pressurized-water nuclear reactor, for the measurement of the flow rate of the pressurized water in that duct.
Figure 4:
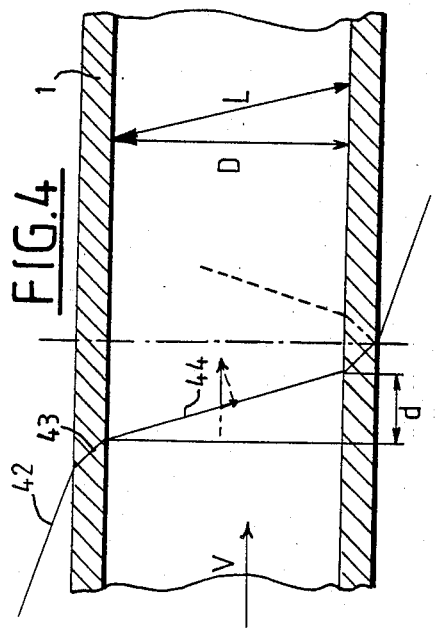
FIG. 4 is a diagrammatic view showing the direction of propagation of the ultrasonic waves in a primary duct of a pressurized-water nuclear reactor.

With reference to FIGS. 3 and 4, an application of the sensor according to the invention to the measurement of the flow rate in a primary duct of a pressurized-water nuclear reactor will now be described. In fact, in order to measure the flow rate in a primary duct 1 of a pressurized-water nuclear reactor, two identical sensors 2 are used, of the type desribed with reference to FIGS. 1 and 2. These two sensors are arranged facing each other separated by a distance d on the duct 1. The supports 21 of these sensors are assembled by cross-pieces such as 32 and are held by clamping straps 25 on the duct 1. The sensors 2 are pivot-mounted, as described before, on the supports 21 in such a way that they can be placed either in operating position 2 or in non-operating position 2' by raising or lowering the handle 35.

One of the sensors 2 emits an ultrasonic wave which propagates in the pressurized water circulating in the ducting in the direction 40, and which is then reflected by the inner wall of the duct to return along direction 41 towards the second sensor 2. The waves also travel in the opposite direction, sensors 2 being both transmitters and receivers. The distance d is determined so as to produce a sufficient echo despite losses during the travel of the waves inside the duct, in order to make it possible to measure the propagation time of the waves between the two sensors in both directions.

Such a measurement makes it possible to determine the velocity of the pressurized water and therefore its flow rate in the duct 1, this method of measuring a flow rate by ultrasonic waves being well known.

Its principle will now be reviewed with reference to FIG. 4.

The ultrasonic waves are emitted in the direction 42, and pass through the wall of the duct 1 in direction 43 and through the pressurized water circulating in this duct 1 in direction 44 and along the path xy. The direction 44 makes an angle $\theta$ with the longitudinal axis of the duct 1 corresponding to the direction of the velocity vector V of the water circulating in the duct. L is the length of the path xy which is greater than the inside diameter of the duct 1. d is the distance along the axial direction of the duct between points x and y.

It can easily be shown, by calculating the propagation time Txy of the waves between x and y and time Tyx of these waves between y and x, that the velocity V of the fluid in the duct can be expressed solely as a function of Txy and Tyx.

This calculation, well known to specialists in the measurement of fluid velocity and flow rate by ultrasonics, shows that:

$$V = 2L^2/d \frac{Txy - Tyx}{(Txy + Tyx)^2}$$

The position of the ultrasonic sensors being determined, the expression $2L^2/d$ is a constant.

V is therefore in the form of a constant which multiplies a propagation time function of the ultrasonic waves between x and y in both directions.

It is therefore very easy to deduce the value of the velocity of the fluid in the duct and its flow rate from the measurement of these propagation times.

This determination of the velocity and that of the flow rate can easily be automated by supplying the propagation times of the waves in both directions in digital form as input data to a computer.

The mounting of sensors shown in FIG. 3 makes it possible to determine the velocity $\vec{V}$ of the fluid in the duct 1 in the same way but with a double-length path for the waves, which increases the accuracy of the measurement.

In addition, the two sensors 2 are arranged on the same generatrix as the duct 1. This placement of the sensors is easier to implement than a placing on diametrically opposite generatrices.

The angle of incidence of the beam of ultrasonic waves in the pressurized water in the duct is of the order of 17° for an initial incidence of the beam 42 ° of 70°. These values of angle of incidence enable the measurements to be made under very good conditions.

The use of a wave guide made of a vitroceramic material in ultrasonic wave sensors enables very good couplings to be made between the piezoelectric pellet and the wall of the duct, while avoiding distortions or expansions of the wave guide in contact with the duct wall at a high temperature, which would be prejudicial to the obtaining of reproducible measurements.

Furthermore, the fitting of the sensor on its support by articulated means such as have been described enables the sensor to be pivoted and access to its bottom surface to be gained without the need to dismantle the clamping of this support on the duct. The sensor can thus be repositioned extremely accurately on the outer wall of the duct.

The wave guide may have a different shape from that which has been described, and it can be mounted in a different way inside the metal body of the sensor. The end of this wave guide must, however, always project slightly from the metal body in order that it alone comes into contact with the wall at a high temperature.

The method of fixing the piezoelectric pellet and the way in which it contacts one of the ends of the wave guide can be different from that which has been described. it is also possible to envisage a means of cooling the inside of the sensor other than a Peltier capsule.

The sensor can be connected in an articulated manner to the support in a different manner to that which has been described, and can in some cases be fixed rigidly to this support, if it is not necessary to inspect its part which comes into contact with the wall at a high temperature.

The wave guide can be made of a vitroceramic material different from that which has been indicated; this vitroceramic material will be selected in accordance with the application for which the sensor is intended and in particular according to the temperature of the wall on which the wave guide will be applied.

The applications of a sensor the wave guide of which is made of a vitroceramic material such as that which has been described are not limited to the measurement of flow rate in a duct of a primary circuit of a pressurized-water nuclear reactor. Such a sensor could be used for other measurements or non-destructive tests through a wall at a temperature much higher than the primary temperature of a pressurized-water nuclear reactor. In fact, the vitroceramic material such as described has characteristics close to those of refractories and can withstand very high temperatures in the order of 1500° C.

Wave guides made of vitroceramic material will always be possible to produce with a very high surface finish, whether this surface finish is produced directly on the cast part or by polishing.

The sensor according to the invention is applicable to any measurement or to any non-destructive test, using ultrasonics, with propagation of ultrasonic waves through a wall at a high temperature.

We claim:

1. In an ultrasonic wave sensor coming into contact with a wall at a high temperature (1), incorporating, within a body (3) made of metallic material connected to a support (21) for positioning the sensor (2) on the wall (1), a piezoelectric ceramic pellet (8) connected on an electrical power supply and/or measuring leads (9), a wave guide a first end of which is placed in contact with said piezoelectric ceramic pellet and a second end (5a) of which is in contact with the wall (1) when the sensor (2) is in operating position, wherein the wave guide (5) consists of a single part made of vitroceramic material, i.e., a material of the glass-type entirely free of any crystal structure in the as-cast state, and developing a crystal structure after treatment, said wave guide being manufactured by casting, crystallization heat treatment, and machining incorporating finishing machining of said second end of said wave guide coming into contact with the wall to a mean roughness of 1 to 6 μm, and perferably to a mean roughness of 3.2 μm.

2. Sensor according to claim 1, wherein the vitroceramic material has approximately the following composition:

Silica $SiO_2$ : 46%
Alumina $Al_2O_3$ : 16%
Magnesia MgO : 17%
Potassium oxide $K_2O$ : 10%
Boron oxide $B_2O_3$ : 7%
Fluorine : 4%

3. Sensor according to claim 1 comprising a Peltier effect capsule (18) fitted in the metallic body, (3) in order to restrict the temperature inside said body (3).

4. Ultrasonic wave sensor according to claim 1, wherein the coupling between the end surface (5a) of the wave guide and the wall (1) is made by means of a coupling material, which consists of an organic material containing nickel powder.

5. Ultrasonic wave sensor according to claim 1, wherein the metal body (3) of the sensor is articulated on a support (30) fixed rigidly with respect to the wall (1) and on the end of a lever (35). itself articulated on the support (30) for moving the sensor, by operating the lever, between an operating position in which the wave guide (5) is in contact with the wall (1) and a non-operating position in which the contact end (5a) of the wave guide is accessible.

6. Ultrasonic wave sensor according to claim 5, wherein the lever (35) is articulated on tne support (30) by means of a link (36).

7. Ultrasonic have sensor according to claim 5, in the case in which the wall (1) consists of the outer wall of a duct, wherein the support (30) is fixed on the duct (1) by means of at least one strap (25) clamped round the duct.

8. Application of an ultrasonic sensor according to claim 1 to the measurement of the flow rate of pressurized water in a primary duct of a pressurized-water nuclear reactor.

9. Application according to claim 8, wherein two identical ultrasonic wave sensors separated by a distance(d) are arranged on the same generatrix of the duct (1).

* * * * *